United States Patent [19]

Nutt et al.

[11] Patent Number: 5,061,693

[45] Date of Patent: Oct. 29, 1991

[54] FIBRINOGEN RECEPTOR ANTAGONISTS

[75] Inventors: Ruth F. Nutt, Green Lane; Stephen F. Brady, Philadelphia; Daniel F. Veber, Ambler, all of Pa.

[73] Assignee: Merck & Co., Inc., Rahway, N.J.

[21] Appl. No.: 386,533

[22] Filed: Jul. 28, 1989

[51] Int. Cl.$^5$ .......................... A61K 37/02; C07K 7/06
[52] U.S. Cl. ......................................... 514/17; 530/329
[58] Field of Search ...................... 514/18, 17; 530/329

[56] References Cited

U.S. PATENT DOCUMENTS

| | | |
|---|---|---|
| 4,578,079 | 3/1986 | Ruoslahti et al. . |
| 4,589,881 | 5/1986 | Pierschbacher et al. . |
| 4,614,517 | 9/1986 | Ruoslahti et al. . |
| 4,683,291 | 7/1987 | Zimmerman et al. . |
| 4,829,051 | 5/1989 | Cort et al. . |
| 4,857,508 | 8/1989 | Adams et al. ........................ 514/18 |

FOREIGN PATENT DOCUMENTS

| | | |
|---|---|---|
| 341915 | of 0000 | European Pat. Off. . |
| WO 39/05150 | 6/1989 | World Int. Prop. O. . |

OTHER PUBLICATIONS

The Merck Index, pp. 145, 1183–1184, 11th edition.
Stryer, "Biochemistry", 3rd Ed., W. H. Freeman & Co., N.Y. (1988), pp. 277–278.
Phillips et al., *Blood*, vol. 71, No. 4, Apr. 1988, pp. 831–843.
Pierschbacher et al., *The J. of Biol. Chem.*, vol. 262, No. 36 (1987), pp. 17294–17298.
Ruoslahti et al., *Science*, vol. 238, Oct. 23, 1987, pp. 491–497.
Plow et al., *Proc. Natl. Acad. Sci. USA*, vol. 82 (1985), pp. 8057–8061.
Pierschbacher et al., Proc. Natl. Acad. Sci. USA, vol. 81 (1984), pp. 5985–5988.
Ruggeri et al., *Proc. Natl. Acad. Sci.*, 1986, vol. 83, pp. 5708–5712.

*Primary Examiner*—Lester L. Lee
*Assistant Examiner*—Stephen B. Maebius
*Attorney, Agent, or Firm*—Charles M. Caruso; Richard S. Parr

[57] ABSTRACT

A fibrinogen receptor antagonist compound of the structure:

$$A-B-C-Gly-Asp-D-E \qquad (I)$$

wherein A, B, C, D and E are preferably defined as follows:
 A is L-asparagine, D-asparagine or acylated asparagine
 B is an L-or D-isomer of proline, thioproline, $\beta,\beta$-dimethylthioproline, or N-methylalanine;
 C is arginine;
 D is phenylalanine, tryptophan $\alpha$-naphthylalanine, $\beta$-napthlalanine, arginine or lysine; and
 E is OH.

10 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the IIb-/IIIa fibrinogen receptor site. Fibrinogen is a glycoprotein, present in blood plasma, which participates in platelet aggregation and in fibrin formation. Platelets are cell-like anucleated fragments, found in the blood of all mammals, which participate in blood coagulation. Interaction of fibrinogen with the IIb/IIIa receptor site is known to be essential for normal platelet function.

When a blood vessel is damaged, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa complex.

Attempts have been made to use natural products and synthetic peptides to study the mechanism of platelet aggregation and adhesion.

Rouslahti and Pierschbacher, Science, 1987, 238, pp. 491–497, describe adhesive proteins such as fibronectin, vitronectin, osteopontin, collagens, thrombospondin, fibrinogen, and von Willebrand factor present in extracellular matrices and in the blood. The proteins contain the tripeptide arginine-glycineaspartic acid as their cell recognition site. The tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh, Proc. Nat'l. Acad. Sci. USA, 1987, 84, pp. 6471–6475, describes an Arg-Gly-Asp directed adhesion receptor expressed by human endothelial cells that is structurally similar to the IIb/IIIa complex on platelets but antigenically and functionally distinct. The receptor is directly involved in endothelial cell attachment to fibrinogen, von Willebrand factor, and vitronectin.

Pierschbacher and Rouslahti, J. of Biol. Chem., 1987, 262, 36, pp. 17294–17298 describe stereochemical influence of the sequence Arg—Gly—Asp—Xaa, where Xaa is one of the 20 natural L-amino acids other than Met, Cys, His, Trp or Gly on binding specificity of peptides containing the tripeptide sequence Arg—Gly—Asp. In Proc. Nat'l. Acad. Sci. USA, 1984, 81, pp. 5985–5988, the same authors describe variants of the cell recognition site of fibronectin that retain attachment-promoting activity. The tetrapeptide Arg—Gly—Asp—Ser is described as the minimal structure recognized by cells in the large, adhesive glycoprotein fibronectin. Peptides having portions —Arg—Gly—Asp—Ser— are described in U.S. Pat. Nos. 4,589,881 and 4,614,517. Peptides having portions —Arg—Gly—Asp—R wherein R is selected from Thr or Cys or other amino acid having the same cell-attachment activity as fibronectin, are described in U.S. Pat. No. 4,578,079.

Ruggeri et al., Proc. Nat'l. Acad. Sci. USA, 1986, 83, pp. 5708–5712, describes a series of synthetic peptides, designed in lengths to 16 residues, that contain the sequence Arg—Gly—Asp—Val, which inhibit fibrinogen binding to platelets.

While it is known that the tripeptide sequence Arg—Gly—Asp is present in certain polypeptides which can duplicate or inhibit the cell attachment-promoting effects of fibronectin and vitronectin, the tripeptide Arg—Gly—Asp has low activity. There is little understanding of the influence on binding specificity of other amino acids in the polypeptide. Applicants have prepared small linear pentapeptides which contain the tripeptide sequence Arg—Gly—Asp which are active platelet aggregation inhibitors.

SUMMARY OF THE INVENTION

The present invention is a fibrinogen receptor antagonist compound of the following structure:

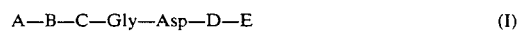

A—B—C—Gly—Asp—D—E    (I)

wherein:

A is any L- or D-isomer of a α-amino acid, an acylated α amino acid, a des-α-amino acid, or an N-methyl-α amino acid;

B is an L-isomer of a secondary amino acid selected from the group consisting of proline, hydroxyproline, thioproline, β,β-dimethylthioproline, dehydroproline, pipecolic acid, azetidine carboxylic acid and N-methyl amino acids;

C is an L-isomer of arginine, homo-arginine, guanido aminobutyric acid, or guanido aminopropionic acid;

D is an L-isomer of tryptophan, phenylalanine, leucine, valine, isoleucine, napthylalanine, methionine, tyrosine, or ring substituted derivatives of tryptophan, tyrosine, phenylalanine, arginine, homo-arginine, ornithine, lysine or histidine; and E is OH, NH$_2$, NHR, NR$_1$R$_2$, wherein R is an alkyl group having 1 to 4 carbon atoms, and R$_1$R$_2$ represents an alkyl group having 1 to 4 carbon atoms, a secondary amino acid, or

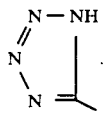

Preferred compounds are those where E is OH.
More preferred compounds are those where:
A is L-asparagine, D-asparagine or acylated asparagine;
B is an L-isomer of proline, thioproline, β,β-dimethylthioproline, or N-methylalanine;
C is arginine;
D is phenylalanine or tryptophan; and
E is OH.

More preferred compounds are:
i) Asn—Pro—Arg—Gly—Asp—Phe—OH,
ii) Asn—ThioPro—Arg—Gly—Asp—Phe—OH,
iii) Asn—(β,β—dimethylThioPro)—Arg—Gly—Asp—Phe—OH,
iv) (D—Asn)—Pro—Arg—Gly—Asp—Phe—OH,
v) (AcAsn)—Pro—Arg—Gly—Asp—Phe—OH,
vi) Asn—Pro—Arg—Gly—Asp—Trp—OH,
vii) Asn—ThioPro—Arg—Gly—Asp—Trp—OH, viii) Asn—(β,β—dimethylThioPro)—Arg—Gly—Asp—Trp—OH,
ix) Asn—(N—methylAla)—Arg—Gly—Asp—Trp—OH,
x) Ser—Sar—Arg—Gly—Asp—Phe—OH,
xi) Asn—Hypro—Arg—Gly—Asp—Phe—OH,
xii) Asn—dehypro—Arg—Gly—Asp—Phe—OH,
xiii) Asn—(D—Arg)—Arg—Gly—Asp—Phe—OH,
xiv) Asn—His—Arg—Gly—Asp—Phe—OH,
xv) Asn—Pro—(D—Arg)—Gly—Asp—Phe—OH,
xvi) Asn—Pro—(D—Arg)—Gly—Asp—Phe—NH$_2$,
xvii) Asn—Pro—Arg—Gly—MeAsp—Phe—OH,
xviii) Gly—Pro—Arg—Gly—Asp—Phe—OH,
xix) Arg—Pro—Arg—Gly—Asp—Phe—OH,
xx) Ala—Pro—Arg—Gly—Asp—Phe—OH,
xxi) Ser—Pro—Arg—Gly—Asp—Phe—OH,
xxii) (D—Asn)—Pro—Arg—Gly—Asp—Phe—OH,
xxiii) Ile—Pro—Arg—Gly—Asp—Phe—OH,
xxiv) Pro—Pro—Arg—Gly—Asp—Phe—OH,
xxv) His—Pro—Arg—Gly—Asp—Phe—OH,
xxvi) Gln—Pro—Arg—Gly—Asp—Phe—OH,
xxvii) Phe—Pro—Arg—Gly—Asp—Phe—OH,
xxviii) Leu—Pro—Arg—Gly—Asp—Phe—OH,
xxix) Asp—Pro—Arg—Gly—Asp—Phe—OH,
xxx) Met—Pro—Arg—Gly—Asp—Phe—OH,
xxxi) (D—N—methyl—Ala)—Pro—Arg—Gly—Asp—Phe—OH,
xxxii) (N—methyl—Ala)—Pro—Arg—Gly—Asp—Phe—OH,
xxxiii) Acetyl—Asn—Pro—Arg—Gly—Asp—Phe—OH,
xxxiv) Asn—Pro—Arg—Gly—Asp—Met—OH,
xxxv) Asn—Pro—Arg—Gly—Asp—Val—OH,
xxxvi) Asn—Pro—Arg—Gly—Asp—Trp—OH(For),
xxxvii) Asn—Pro—Arg—Gly—Asp—Trp—OH,
xxxviii) Asn—Thio Pro—Arg—Gly—Asp—Trp—OH,
xxxix) Asn—Azt—Arg—Gly—Asp—Trp—OH,
xxxx) Asn—Pip—Arg—Gly—Asp—Trp—OH,
xxxxi) Asn—(D—Pip)—Arg—Gly—Asp—Trp—OH,
xxxxii) Asn—(N—methyl—Ala)—Arg—Gly—Asp—Trp—OH,
xxxxiii) Asn—(N—methyl—Phe)—Arg—Gly—Asp—Trp—OH,
xxxxiv) Asn—(D—Arg)—Arg—Gly—Asp—Trp—OH and
xxxxv) Asn—His—Arg—Gly—Asp—Trp—OH.

Unless otherwise indicated, each amino acid is the L-isomer.

More preferred compounds are:
ii) Asn—ThioPro—Arg—Gly—Asp—Phe—OH,
iii) Asn—(β,β-dimethylThioPro)—Arg—Gly—Asp—Phe—OH,
vi) Asn—Pro—Arg—Gly—Asp—Trp—OH,
vii) Asn—ThioPro—Arg—Gly—Asp—Trp—OH, and
ix) Asn—(N-methylAla)—Arg—Gly—Asp—Trp—OH.

The invention also includes compositions, comprising fibrinogen receptor antagonist peptides of the present invention and one or more pharmacologically acceptable carriers, e.g. saline, at a pharmacologically acceptable pH, e.g. 7.4, which are suitable for continuous intravenous or oral intravenous bolus administration for promoting inhibition of platelet aggregation.

The invention also includes methods for inhibiting platelet aggregation which comprise administering to a patient, either by continuous intravenous or oral intravenous bolus method, an effective amount of a composition of the present invention.

DETAILED DESCRIPTION OF THE INVENTION

Compounds of the invention are fibrinogen receptor antagonists which inhibit fibrinogen induced platelet aggregation. These compounds are prepared by solid phase synthesis which is well known in the art, or by liquid phase synthesis which is well known in the art. The methods of synthesis are generally described by Neurath, Hill and Boeder, Eds. "The Proteins" 3rd Edition, Volume II, Academic Press 1976.

The compounds have a relatively short duration of activity which makes them desirable for use in therapeutic treatments where prevention of platelet aggregation over a short period of time is desirable. The compounds are also particularly advantageous because they do not significantly deplete the platelet count.

An essential feature of the compounds of the present invention is the presence of an L-isomer of a secondary amino acid selected from the group consisting of proline thioproline, β,β-dimethylthio-proline, dehydroproline, pipecolic acid, azetidine carboxylic acid or an N-methylamino acid at position B of the compound formula. While applicants do not wish to be bound to any particular theory, the presence of a secondary amino acid at position B is believed to affect the conformation of the compound such that it is readily recognized and accepted by the IIb/IIIa receptor site, thereby enhancing its potency.

Common or α-amino acids are the twenty with which all proteins in all species, from bacteria to humans are constructed.

| Common Amino Acids | | | |
|---|---|---|---|
| Amino Acid | Abbreviation | Amino Acid | Abbreviation |
| Alanine | Ala | Leucine | Leu |
| Arginine | Arg | Lysine | Lys |
| Asparagine | Asn | Methionine | Met |
| Aspartic Acid | Asp | Phenylalanine | Phe |
| Cysteine | Cys | Proline | Pro |
| Glutamine | Gln | Serine | Ser |
| Glutamic Acid | Glu | Threonine | Thr |
| Glycine | Gly | Tryptophan | Trp |
| Histidine | His | Tyrosine | Tyr |
| Isoleucine | Ile | Valine | Val |

Compounds of the invention may be prepared using solid phase peptide synthesis, such as that described by Merrifield, J. Am. Chem. Soc., 85, 2149 (1964), although other equivalent chemical syntheses known in the art can also be used, such as the syntheses of Houghten, Proc. Natl. Acal. Sci., 82, 5132 (1985). Solid-phase synthesis is commenced from the C-terminus of the peptide by coupling a protected amino acid to a suitable resin, as generally set forth in U.S. Pat. No. 4,244,946, issued Jan. 21, 1982 to Rivier et al., the disclosure of which is hereby incorporated by reference. Examples of synthesis of this general type are set forth in U.S. Pat. Nos. 4,305,872 and 4,316,891. Compounds of the invention can also be prepared according to liquid phase synthesis described by Neurath, Hill and Boeder, Eds., "The Proteins" 3rd Edition, Vol. II, Chapter 2 pp. 106-252.

In synthesizing these polypeptides, the carboxyl terminal amino acid, having its alpha-amino group suitably protected, is coupled to a chloromethylated polystyrene resin or the like. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in the open literature.

The remaining alpha-amino- and side-chain-protected amino acids are then coupled by condensation stepwise in the desired order to obtain an intermediate compound connected to the resin.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, N-hydroxysuccinic acid imido ester methods, cyanomethyl ester method, etc.), Woodward reagent K method, carbonyldiimidazol method, oxidation-reduction method or BOP benzotriazole-1-yloxytris (dimethylamino) phosphonium hexafluorophosphate) method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of the alpha-amino group on an amino acid or a fragment while that entity reacts at the carboxyl group followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the alpha-and omega-side chain amino groups are exemplified such as benzyloxycarbonyl (hereinafter abbreviated as Z), isonicotinyloxycarbonyl (iNOC), o-chlorobenzyloxycarbonyl [Z(2-Cl)], p-nitrobenzyloxycarbonyl [Z(NO₂)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified, for example, benzyl ester (OBzl), 4-nitrobenzyl ester (ONb), t-butyl ester (OBut), cyclohexyl (Chx), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenylsulfonyl (Mts), and the like. The thiol group in cysteine may be protected with benzyl, p-methoxybenzyl, triphenylmethyl, acetylaminomethyl, ethylcarbamoyl, 4-methylbenzyl, 2,4,6-trimethylbenzyl (Tmb) etc., and the hydroxyl group in serine can be protected with benzyl, t-butyl, acetyl, tetrahydropyranyl etc.

Stewart and Young, "Solid Phase Peptide Synthesis", Pierce Chemical Company, Rockford, IL (1984) provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151. These descriptions are hereby incorporated by reference.

After the desired amino-acid sequence has been completed, the intermediate peptide is removed from the resin support by treatment with a reagent, such as liquid HF, which not only cleaves the peptide from the resin, but also cleaves all the remaining side-chain protecting groups. The polypeptide can then be purified by gel permeation followed by semipreparative HPLC, as described in Rivier et al., Peptides: Structure and Biological Function (1979) pp. 125–128.

EXAMPLE 1

Synthesis of
H—Asn—Pro—Arg—Gly—Asp—Phe—OH

Starting with 0.5 mM of Boc—Phe—O—Pam—resin:

$$(CH_3)_3C-O-\overset{O}{\underset{\|}{C}}-NH-CH-\overset{CH_2-Ph}{\underset{|}{C}}-O-CH_2-Ph-CH_2\overset{O}{\underset{\|}{C}}-NH-CH_2-[pcr]$$

wherein "pcr" is a polystyrene crosslinked resin, the alpha-amino Boc protecting group (tert-butyloxy-carbonyl) is removed using trifluoroacetic acid and methylene chloride, and the deprotected phenylalanine neutralized with diisopropylethyl amine.

Two mM Boc-protected Asp (benzyl ester) (Asp-(OBzl)) is then coupled to phenylalanine mediated by 1 mM dicyclohexylcarbodiimide, deprotected using trifluoroacetic acid and methylene chloride, and neutralized with diisopropylethylamine.

Two mM Boc-protected Gly is then coupled to Asp (benzyl ester) mediated by 1 mM dicyclohexylcarbodiimide, deprotected and neutralized as described above.

Two mM Boc-protected Arg (4-toluenesulfonyl) (Arg(Tos)) is then coupled to glycine mediated by 2 mM dicyclohexylcarbodiimide and 2 mM 1-hydroxybenzo-triazole, deprotected and neutralized as described above.

Two mM Boc-protected Pro is then coupled to Arg (4-toluenesulfonyl) mediated by 1 mM dicyclohexylcarbodiimide, deprotected and neutralized as described above.

Two mM Boc-protected Asn is then coupled to Pro mediated by 2 mM dicylohexylcarbodiimide and 2 mM 1-hydroxybenzotriazole. Trifluoroacetic acid and methylene chloride are added to deprotected Asn to form the following salt:

$$\text{TFA salt.Asn—Pro—}\overset{\text{Tos}}{\overset{|}{\text{Arg}}}\text{—Gly—}\overset{\text{Bzl}}{\overset{|}{\text{Asp}}}\text{—Phe—O—Pam—}\textcircled{R}$$

Cleavage of the peptide from the resin is achieved using HF/anisole (9:1 (v/v)), to form HF salt H.Asn—Pro—Arg—Gly—Asp—Phe—OH Purification is conducted using preparative HPLC in 0.1% TFA $H_2O$—$CH_3CN$ gradient. The final TFA salt product is converted to HOAc salt by passing through ion exchange column BioRad AG3-X4A (acetate cycle).

Therapeutic Utility

Peptides of the invention may be used for inhibiting integrin protein-complex function relating to cell-attachment activity. For example, they may be administered to patients where inhibition of human or mammalian platelet aggregation or adhesion is desired.

Polypeptides of the invention are eliminated from circulation rapidly and are particularly useful in inhibiting platelet aggregation in situations where a strong antithrombotic of short duration of effectiveness is needed. Thus, they may find utility in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Polypeptides of the invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol., 1987, 252:H, pp 615-621). Platelets released from artificial surfaces show impaired hemostatic function. Polypeptides of the invention may be administered to prevent adhesion.

Other applications of these polypeptides include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures. Polypeptides of the invention may also be used to prevent myocardial infarction.

These polypeptides may be administered by any convenient means which will result in its delivery into the blood stream in substantial amount including continuous intravenous or bolus injection or oral methods. Compositions of the invention include peptides of the invention and pharmacologically acceptable carriers, e.g. saline, at a pH level e.g. 7.4, suitable for achieving inhibition of platelet aggregation. They may be combined with thrombolytic agents such as plasminogen activators or streptokinase in order to inhibit platelet aggregation. They may also be combined with anticoagulants such as heparin, aspirin or warfarin. Intravenous administration is presently contemplated as the preferred administration route. They are soluble in water, and may therefore be effectively administered in solution.

In one exemplary application, a suitable amount of peptide is intravenously administered to a heart attack victim undergoing angioplasty. Administration occurs during or several minutes prior to angioplasty, and is in an amount sufficient to inhibit platelet aggregation, e.g. an amount which achieves a steady state plasma concentration of between about 0.05-30 $\mu M$ per kilo, preferably between about 0.3-3 $\mu M$ per kilo. When this amount is achieved, an infusion of between about 1-100 $\eta M$ per kilo per min., preferably between about 10-30 $\eta M$ per kilor per min. is maintained to inhibit platelet aggregation. Should the patient need to undergo bypass surgery, administration may be stopped immediately and will not cause complications during surgery that would be caused by other materials such as aspirin or monoclonal antibodies, the effects of which last hours after cessation of administration.

The present invention also includes a pharmaceutical composition comprising peptides of the present invention and tissue-type plasminogen activator or streptokinase. The invention also includes a method for promoting thrombolysis and preventing reocclusion in a patient which comprises administering to the patient an effective amount of compositions of the invention.

The present invention may be embodied in other specific forms without departing from the spirit or essential attributes thereof. Thus, the specific examples described above should not be interpreted as limiting the scope of the present invention.

What is claimed is:

1. A fibrinogen receptor antagonist compound of the formula:

$$A-B-C-Gly-Asp-D-E \qquad (I)$$

wherein:

A is L-asparagine, D-asparagine or acylated asparagine;

B is an L-isomer of a secondary amino acid selected from the group consisting of proline, hydroxy proline, thioproline, β,β-dimethylthioproline, dehydroproline, pipecolic acid, and azetidine carboxylic acid and N-methyl amino acids;

C is an L-isomer of arginine, homo-arginine, guanido aminobutryic acid, or guanido aminopropionic acid;

D is tryptophan or phenylalanine; and

E is OH, $NH_2$, NHR, or $NR_1R_2$, wherein R is an alkyl group having 1 to 4 carbon atoms, and wherein $R_1$ and $R_2$ are the same or different and each represents an alkyl group having 1 to 4 carbon atoms.

2. A fibrinogen receptor antagonist of claim 1 wherein:.

A is L-asparagine, D-asparagine or acylated asparagine;

B is an L-isomer of proline, thioproline, β,β-dimethylthioproline, or N-methylalanine;

C is arginine;

D is phenylalanine or tryptophan; and

E is OH.

3. A fibrinogen receptor antagonist of claim 1 which is
   Asn—Pro—Arg—Gly—Asp—Phe—OH.
4. A fibrinogen receptor antagonist of claim 1 which is
   Asn—ThioPro—Arg—Gly—Asp—Phe—OH.
5. A fibrinogen receptor antagonist of claim 1 which is
   Asn—(β,β—dimethylThioPro)—Arg—Gly—Asp—Phe—OH.
6. A fibrinogen receptor antagonist of claim 1 which is
   (D—Asn)—Pro—Arg—Gly—Asp—Phe—OH.
7. A fibrinogen receptor antagonist of claim 1 which is
   (AcAsn)—Pro—Arg—Gly—Asp—Phe—OH.
8. A fibrinogen receptor antagonist of claim 1 which is
   Asn—Pro—Arg—Gly—Asp—Trp—OH.
9. A composition for inhibiting fibrinogen-induced platelet aggregation in a mammal comprising a peptide of claim 1 and a pharmaceutically acceptable carrier.
10. A method for inhibiting fibrinogen binding to mammalian platelets comprising administering to a patient a composition of claim 9.

* * * * *